United States Patent
Schmidt et al.

(10) Patent No.: US 6,875,014 B2
(45) Date of Patent: Apr. 5, 2005

(54) METHOD FOR MONITORING A COMBUSTION PROCESS, AND CORRESPONDING DEVICE

(75) Inventors: Dirk Schmidt, Hattingen (DE); Bernd Beyer, Essen (DE); Franz Wintrich, Essen (DE)

(73) Assignee: Powitec Intelligent Technologies GmbH, Essen (DE)

( * ) Notice: Subject to any disclaimer, the term of this patent is extended or adjusted under 35 U.S.C. 154(b) by 0 days.

(21) Appl. No.: 10/850,244

(22) Filed: May 20, 2004

(65) Prior Publication Data

US 2004/0214123 A1 Oct. 28, 2004

Related U.S. Application Data

(63) Continuation of application No. PCT/EP02/13899, filed on Dec. 7, 2002.

(30) Foreign Application Priority Data

Dec. 7, 2001 (DE) .......................................... 101 60 222

(51) Int. Cl.⁷ .............................. F27B 9/40; F27D 19/00
(52) U.S. Cl. ............................ 432/37; 432/49; 432/112
(58) Field of Search ............................. 432/19, 20, 37, 432/49, 112

(56) References Cited

U.S. PATENT DOCUMENTS

| | | | |
|---|---|---|---|
| 3,578,298 A | * | 5/1971 | Hurlbut et al. ............... 432/17 |
| 3,627,287 A | | 12/1971 | Herz |
| 3,888,621 A | | 6/1975 | Williams |
| 4,062,006 A | * | 12/1977 | Solheim et al. ............. 340/515 |
| 4,077,763 A | | 3/1978 | Jäger et al. |
| 4,115,998 A | * | 9/1978 | Gilbert et al. ........... 60/39.091 |
| 4,424,023 A | * | 1/1984 | Matsuoka ..................... 432/19 |
| 4,675,826 A | * | 6/1987 | Gentry et al. ............... 700/209 |
| 4,716,532 A | | 12/1987 | Benoit et al. |
| 4,948,365 A | * | 8/1990 | Yuen .......................... 432/103 |
| 5,794,549 A | * | 8/1998 | Carter ........................ 110/347 |
| 5,997,288 A | | 12/1999 | Adams |
| 6,113,386 A | * | 9/2000 | Shannon et al. .............. 432/59 |

FOREIGN PATENT DOCUMENTS

| | | |
|---|---|---|
| DE | 2 224 045 | 5/1972 |
| DE | 2 224 049 | 11/1973 |
| DE | 25 15 807 | 10/1975 |
| DE | 25 07 840 | 9/1976 |
| DE | 36 07 261 A1 | 9/1986 |
| DE | 197 10 206 A1 | 9/1998 |
| DE | 199 50 981 A1 | 4/2000 |
| GB | 1 424 364 | 2/1976 |

* cited by examiner

*Primary Examiner*—Gregory Wilson
(74) *Attorney, Agent, or Firm*—Womble Carlyle Sandridge & Rice, PLLC

(57) ABSTRACT

In a method for monitoring a combustion process, in which, in a oven, a substance arranged in a bed of the oven is converted under the supply of heat by way of firing by a flame, data of the flame and/or the substance in the bed being recorded by way of at least one sensor, the input of heat into the bed is determined from the data recorded by the sensor and is used for quality determination.

16 Claims, No Drawings

METHOD FOR MONITORING A COMBUSTION PROCESS, AND CORRESPONDING DEVICE

CROSS-REFERENCE TO RELATED APPLICATION

This is a continuation of PCT/EP02/13899, which was filed Dec. 7, 2002, designates the U.S., and is incorporated herein by reference.

BACKGROUND OF THE INVENTION

1) Field of the Invention

The invention relates to a method for monitoring a combustion process, in which, in a oven, a substance arranged in a bed of the oven is converted under the supply of heat by way of firing by a flame, data of the flame and/or the substance in the bed is recorded by way of at least one sensor, and the input of heat into the bed is determined from the data recorded by the sensor and is used for quality determination, as a result of the thermal radiations of the flame and of the bed being recorded as data by the sensor and normalized by way of the supplied and/or produced quantities of energy and material. The invention also relates to a device for carrying out the method for monitoring the combustion process.

2) Description of Related Art

DE 199 50 981 A1 discloses a rotary tubular kiln for converting a substance, in which spectroscopic data of the fired cement is determined. The intensity of the data, in particular that of calcium hydroxide, is used to draw conclusions as to the clinker index (FCAO) as a measure of the quality of the cement.

U.S. Pat. No. 5,997,288 A describes a method of the type described in the above Field of the Invention section for the heat treatment of coal in an externally heated rotary tubular kiln, in which hot gas is passed through the coal in countercurrent and the temperature of the bed of coal in the oven is measured by means of thermocouples arranged at a central lance, in order to control the input of heat into the bed of coal and the quality of the treated coal.

DE 25 15 807 A1 has likewise disclosed a method of the type described in the above Field of the Invention section, in which petroleum coke is heat-treated in a rotary tubular kiln, with pyrometers measuring the radiation intensity of the coke bed or of the kiln wall.

BRIEF SUMMARY OF SOME ASPECTS OF THE INVENTION

The present invention is based on the object of improving a method and a device of the type described in the above Field of the Invention section. One aspect of the present invention is the provision of a method for monitoring a combustion process, in which, in a oven, a substance arranged in a bed of the oven is converted under the supply of heat by way of firing by a flame, data of the flame and/or the substance in the bed is recorded by way of at least one sensor, and the input of heat into the bed is determined from the data recorded by the sensor and is used for quality determination, as a result of the thermal radiations of the flame and of the bed being recorded as data by the sensor and normalized by way of the supplied and/or produced quantities of energy and material, wherein to control the combustion process the input of heat into the bed is determined from the difference between the normalized thermal radiations of the flame and of the bed and is optimized at a defined temperature.

By virtue of the fact that to control the combustion process, the input of heat into the bed is determined from the difference between the normalized thermal radiations of the flame and of the bed and is optimized at a defined temperature, a measure of the quality of the converted substance which is simpler to determine than the spectroscopic measurement, with the control base thereon, is provided. This is true in particular if the input of heat into the bed or the thermal radiation of the flame and of the bed are recorded optically, i.e. the camera arrangement which is in any case present for flame observation is used. To control the combustion process, it is preferable for the normalized thermal radiations, at a defined temperature, as far as possible to be kept in a constant relationship with respect to one another.

The method and the device of the present invention can be used for all conversion operations in which the conversion, firing, sintering or the like of the substance is dependent on the specific heat input, i.e. for example for the firing of cement or lime or in glassmaking.

DETAILED DESCRIPTION OF THE INVENTION

In the text which follows, the invention is explained in more detail on the basis of an exemplary embodiment.

The interior of a cement oven designed as a rotary tubular kiln has a bottom region, which is referred to as the bed, sintering zone or clinker bed. During the combustion process, the finished cement is formed in the bed. Above the bed is the region in which, during the combustion process, the flame is formed. The thermal radiation $S_F$ of the flame, the thermal radiation $S_B$ of the cement formed in the bed, the thermal radiation $S_Z$ of the cement (clinker) after the flame and the thermal radiation $S_W$ of the rotary tubular kiln wall are recorded at a plurality of locations and for a prolonged period of time by way of a plurality of thermal radiation sensors. Examples of the sensors are a multichip CCD camera, a CMOS camera or a glass fiber camera with a plurality of glass fibers which are independent of one another, in each case with connected image processing, and the data is fed to a computer.

The absolute values for the thermal radiation are then also normalized. Specifically, the thermal radiations $S_F$ and $S_W$ of the flame and the rotary tubular kiln wall are normalized using the quantity and quality of the fuel, i.e. the calorific value $M_B$. Similarly, the thermal radiations $S_B$ and $S_Z$ of the bed and the cement are normalized using the quantity of clinker produced (cement quantity) $M_Z$. A control performed by the computer, for example by way of a neural network, uses a function of these different normalized thermal radiations, i.e.

$$f(S_F/M_B, S_W/M_B, S_B/M_Z, S_Z/M_Z).$$

The combustion process is controlled in such a way that at a defined temperature a relationship which is as constant as possible is maintained between these normalized thermal radiations.

The difference between the normalized thermal radiation $S_F/M_B$ of the flame and the normalized thermal radiation $S_B/M_Z$ of the bed substantially determines the input of heat $Q_B$ into the bed, i.e. the quantity of heat supplied to the bed. The FCAO value, which is a measure of the quality of the cement, is directly dependent on this (specific) heat input $Q_B$ into the bed, in which context the quality may locally differ on account of the locally dependent nature of the input of heat $Q_B$. Therefore, the control of the combustion process is intended to achieve the maximum input of heat $Q_B$ into the bed. For this purpose, the computer controls various actuating devices which determine the control variables of the oven, for example the supply of air, fuel, lime and aggregates.

What is claimed is:

1. A method for monitoring a combustion process in which there is a quantity of energy supplied so that a substance arranged in a bed of an oven is converted under the supply of heat by way of firing by a flame to produce a quantity of produced material, the method comprising:
    recording data through the use of at least one sensor, with the recorded data including at least:
        thermal radiation data for the flame, and
        thermal radiation data for the substance in the bed;
    normalizing data, through the use of one or more quantities selected from the group consisting of the quantity of energy supplied and the quantity of produced material, to produce normalized data,
        wherein the data being normalized includes at least:
            the thermal radiation data for the flame and,
            the thermal radiation data for the substance in the bed, and
        whereby the normalized data includes at least:
            normalized thermal radiation data for the flame, and
            normalized thermal radiation data for the substance in the bed;
    determining a quantity of heat input into the bed from a difference between the normalized thermal radiation data for the flame and the normalized thermal radiation data for the substance in the bed;
    determining a quality using the quantity of heat input into the bed; and
    controlling the combustion process, wherein the controlling of the combustion process includes optimizing the quantity of heat input into the bed at a defined temperature.

2. The method as claimed in claim 1, wherein the controlling of the combustion process further includes keeping at least the normalized thermal radiation data for the flame and the normalized thermal radiation data for the substance in the bed in a substantially constant relationship with respect to one another.

3. The method as claimed in claim 2, wherein the recording of the data through the use of at least one sensor comprises recording the data through the use of a camera arrangement.

4. The method as claimed in claim 2, wherein during the combustion process the flame is formed above the bed.

5. The method as claimed in claim 1, wherein the recording of the data through the use of at least one sensor comprises recording the data through the use of a camera arrangement.

6. The method as claimed in claim 5, wherein during the combustion process the flame is formed above the bed.

7. The method as claimed in claim 1, wherein during the combustion process the flame is formed above the bed.

8. The method as claimed in claim 1, wherein the determining of the quality comprises determining a quality of the produced material.

9. The method as claimed in claim 1,
    wherein the recorded data further includes:
        thermal radiation data for a wall of the oven, and
        thermal radiation data for the produced material after the flame;
    wherein the data being normalized further includes:
        the thermal radiation data for the wall of the oven, and
        the thermal radiation data for the produced material after the flame;
    whereby the normalized data further includes:
        normalized thermal radiation data for the wall of the oven, and
        normalized thermal radiation data for the produced material after the flame; and
    wherein the controlling of the combustion process further includes keeping at least the normalized thermal radiation data for the flame, the normalized thermal radiation data for the substance in the bed, the normalized thermal radiation data for the wall of the oven, and the normalized thermal radiation data for the produced material after the flame in a substantially constant relationship with respect to one another.

10. A device for monitoring a combustion process in which there is a quantity of energy supplied so that a substance arranged in a bed of an oven is converted under the supply of heat by way of firing by a flame to produce a quantity of produced material, the apparatus comprising:
    at least one sensor for obtaining at least thermal radiation data for the flame and thermal radiation data for the substance in the bed; and a computer operative for:
    receiving at least the thermal radiation data for the flame and the thermal radiation data for the substance in the bed;
    normalizing data, through the use of one or more quantities selected from the group consisting of the quantity of energy supplied and the quantity of produced material, to produce normalized data,
        wherein the data being normalized includes at least:
            the thermal radiation data for the flame and,
            the thermal radiation data for the substance in the bed, and
        whereby the normalized data includes at least:
            normalized thermal radiation data for the flame, and
            normalized thermal radiation data for the substance in the bed;
    determining a quantity of heat input into the bed from a difference between the normalized thermal radiation data for the flame and the normalized thermal radiation data for the substance in the bed; and
    determining a quality using the quantity of heat input into the bed.

11. The device as claimed in claim 10, wherein the computer is further operative for controlling the combustion process in the oven.

12. The device as claimed in claim 11, wherein a neural network is implemented in the computer for control purposes.

13. The device as claimed in claim 11, wherein the computer is operative so that the controlling of the combustion process includes optimizing the quantity of heat input into the bed at a defined temperature.

14. The device as claimed in claim 13, wherein the computer is operative so that the controlling of the combustion process further includes keeping at least the normalized thermal radiation data for the flame and the normalized thermal radiation data for the substance in the bed in a substantially constant relationship with respect to one another.

15. The device as claimed in claim 13, wherein the computer is operative so that the determining of the quality comprises determining a quality of the produced material.

16. The device as claimed in claim 10, wherein the sensor comprises a camera arrangement.

* * * * *